United States Patent [19]

Esposito

[11] Patent Number: 5,405,869
[45] Date of Patent: Apr. 11, 1995

[54] ANTI-TUMOR PLATINUM COMPLEXES

[75] Inventor: Mauro Esposito, Genoa, Italy

[73] Assignee: Istituto Nazionale per la Ricerca sul Cancro, Genoa, Italy

[21] Appl. No.: 185,830

[22] PCT Filed: Jul. 17, 1992

[86] PCT No.: PCT/EP92/01623

§ 371 Date: Feb. 22, 1994

§ 102(e) Date: Feb. 22, 1994

[87] PCT Pub. No.: WO93/03046

PCT Pub. Date: Feb. 18, 1993

[30] Foreign Application Priority Data

Jul. 26, 1991 [IT] Italy ............................ MI91A2072

[51] Int. Cl.$^6$ .................... C07F 15/00; A61K 31/28
[52] U.S. Cl. ................................ 514/492; 556/137
[58] Field of Search ....................... 556/137; 514/492

[56] References Cited

FOREIGN PATENT DOCUMENTS 0328274 8/1989 European Pat. Off. .
0212497 8/1990 Japan .

OTHER PUBLICATIONS

Craciunescu et al., Eur. J. Med. Chem.-Chim. Ther., vol. 19, No. 4, pp. 353–357 (1984).
Patent Abstract of Japan, vol. 13, No. 145, C583, abstract of JP 63-303987 (1988).

Primary Examiner—José G. Dees
Assistant Examiner—Porfirio Nazario-gonzalez
Attorney, Agent, or Firm—Bucknam and Archer

[57] ABSTRACT

Compounds of formula (1):

$$(a_m)_2 Pt \; O-CO-C_6H_4-NH_2(p), (Cl)_n (HCl)_n \atop (ROH)_m \qquad (1)$$

in which $a_m$ is a monovalent amine ligand which is $NH_3$, a linear or branched $C_1$–$C_6$ alkylamine, a cyclic amine of 3–6 carbon atoms, or the two $a_m$ groups form a linear or cyclic $C_{2-8}$-alkyl-1,2 diamine or 1,3-diamine; R is hydrogen or $C_{1-3}$ alkyl; $n_1$, and m are independently zero or 1 and n is 1, are active in the treatment of several tumors, including tumor of ovary, breast, lungs, melanoma, microcytoma.

8 Claims, No Drawings

ANTI-TUMOR PLATINUM COMPLEXES

The present invention refers to platinum(II) complexes of formula (1)

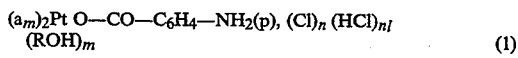
$$(a_m)_2\text{Pt O—CO—C}_6\text{H}_4\text{—NH}_2(p), (Cl)_n (HCl)_{n1} (ROH)_m \quad (1)$$

wherein:
$a_m$ is a monovalent amine ligand, selected from $NH_3$, linear or branched $C_1$–$C_6$ alkylamine, cyclopentylamine, a cyclic amine such as cyclopropylamine or cyclohexylamine; or the two a groups form a linear or cyclic $C_{2-8}$-alkyl-1,2 or 1,3-diamine;
R is hydrogen or $C_{1-3}$ alkyl;
$n_1$, n and m are independently zero or the integer 1.

The linear or branched $C_{1-5}$ alkylamine is preferably isopropylamine, propylamine or n-pentylamine; the linear or branched $C_{1-3}$ dialkylamine is preferably diisopropylamine.

Examples of linear $C_{2-8}$-alkyl-1,2- or 1,3-diamine include 1,2-ethylenediamine, (R, S, racemic or meso)-butane-1,2-diamine, 1,3-propylenediamine; examples of cyclic diamine comprise R, S, racemic or meso cyclopentane-1,2-diamine; R, S, (racemic or meso) cyclohexane-1,2-diamine; 1,1-bis-aminomethyl-cyclopentane; 1;1-bisaminomethylcyclohexane.

When m is 1, the compounds (1) are solvates with water or alcohols.

When $n_1$ is 1, the compounds (1) are addition salts. Particularly preferred compounds are: cis-diaminochloro-(4-amino)benzoate-platinum(II), cis-diaminochloro-(4-amino)benzoate-platinum(II) hydrochloride, (1A) aquo-cis-diamino-chloro-(4-amino)benzoate-platinum(II), (1B) cis-diamino-chloro-(4-amino)benzoate-platinum(II) mono methanol solvate, (1C).

The compounds of formula (1) are prepared by a process comprising:
a) the reaction of a dichloro platinum(II) complexes of formula (2)

wherein $a_m$ is a defined above, with at least one molar equivalent of p-aminobenzoic acid in the form of free acid or of carboxylate salt with a mono or bivalent metal, preferably alkali, alkaline-earth metal or silver, in a suitable hydroxylated solvent;
b) the subsequent purification of a compound of formula (1).

Preferred solvents are water, $C_{1-3}$ alcohols or mixtures thereof. Water solutions or suspensions of reagents are particularly preferred.

It is particularly preferred the use of lithium p-aminobenzoate which is more easily handled and less toxic than the silver or barium salts.

The reaction may be carried out by mixing water solutions of the reagents or adding a dichloroplatinum-(II) of formula (2) as finely subdivided solid to a water solution of p-aminobenzoic acid in form of free acids or its salts. The mixture is stirred for a period ranging from some hours to some days, at temperature from the room temperature to the reflux temperature.

Preferred temperatures are comprised from 50° to 80° C. for a period from 1 and 24 hours.

At least one molar equivalent of p-aminobenzoic acid or of its salt is used per mole of platinum complex (2); the use of an excess amount increases the reaction rate.

The purification of compounds (1) may be carried out by precipitation as hydrochloride salts by dilution of an aqueous solution with concentrated hydrochloric acid; or by silica gel column chromatography or by repeated crystallizations from an alcoholic solvents, e.g. methanol.

The dichloro platinum complexes (2) are commercially available or they are known or they may be prepared by known methods.

The compounds (1), particularly in the salified form, are characterized by a good or very good water solubility (e.g.: 1A 7 mg/ml; 1C>3 mg/ml), and the solutions in water or in HCl 0.01N have a remarkable stability (12–24 hours at least at room temperature). The compounds (1) have a low toxicity; for example the $LD_{50}$ for 1B and 1C is higher than 240 mg/kg was surprisingly higher than 1200 mg/kg for 1A. The low toxicity is combined with a low or irrelevant nephrotoxicity as shown by the BUN value of 36±8 mg/100 ml, after a cumulative dose of 1200 mg/kg of compound 1A, and measured at the $8^{th}$ day after the end of the treatment.

The evaluation of the cytotoxic activities of the compounds (1) was carried out "in vitro" measuring, according to known methods, the inhibition of the colony formation, the cell viability (Trypan blu) and the incorporation of tritiated thymidine in tumoral and normal cells.

For instance, compound 1A cis-diamino-chloro-(4-amino)benzoate-platinum(II) hydrochloride inhibits the "in vitro" growth of leukemia cells P388, K562 and Jurkat ($ID_{50}$ measured by incorporation of tritiated thymidine at 48 hours of 11.4, 26.3 and 21.3 μM, respectively) and has significant cytotoxic activity on cells of solid tumors, such as ovary (SW626), breast (MCF-7 and MDA), lung (A549), melanoma (SKMEL-26), microcytoma (GCLI) as well as on non tumoral stabilized EBV+ cell lines, both B95-8 (marmoset) and from patients affected by acute or chronic mononucleosis.

The "in vivo" cytotoxic activity of the compounds of the invention was determined by measuring survival of BDF1 mice inoculated i.p. with $10^5$ cells of P388, in comparison with untreated controls.

The compounds (1) were administered at increasing doses, according to different therapeutic schemes.

The efficacy of the compounds is dose-dependent and is strictly related to the cumulative administered dose. The compounds (1) are therefore particularly advantageous and useful for the treatment of tumors sensitive to platinum complexes both because of their high water solubility and of their intrinsic low general toxicity and nephrotoxicity.

The effective dosage of the compounds of the invention may be determined by a skilled physician with known methods. The correlation between the dosages used in animals of various species and sizes and those used in human (according to mg/m² of body surface) is disclosed by Freirech, E. J. et al., in Cancer Chemother. Rep., 50, 4, 219–244; 1966.

Usually, doses from 1 to 1200 mg/kg of the complexes will be administered, with a dosage regimen changing according to various factors.

The treatment regimen may be suitably changed according to the kind of tumor and to the patients conditions. The compound of the invention are preferably administered as sterile aqueous solutions, preferably by intravenous or intraarterial route although other administration routes may be convenient in particular cases.

The pharmaceutical forms which may be used for the parenteral administration comprise sterile aqueous solutions or sterile powders for the extemporaneous preparation of the solutions as well as oily preparations by intramuscular or intraperitoneal administration.

Other useful pharmaceutical forms may be syrup or similar liquid forms, as well as solid forms such as tablets, capsules or the like.

The preparation of the compounds of the invention is shown in the following examples.

EXAMPLE 1

0.66 mol of p-aminobenzoic acid (PABA) finely divided are added under stirring to a solution of cis-diamino-dichloro-platinum(II) (0.33 mol) in water (25 ml). The mixture is heated to 80° C. and, kept at this temperature for 20 hours under stirring. After filtration and cooling to room temperature, the mixture is added with 10 ml of concentrated hydrochloric acid.

By subsequent cooling for 24 hours at 0°–4° C., a crystalline precipitate of cis-diamino-chloro-(4-amino)-benzoate-platinum(II) hydrochloride 1A is separated, which is filtered.

The crystalline product is washed with ethyl ether and dried at room temperature under vacuum.

If desired, the product may be re-crystallized by treatment of a solution of 0.09 g of cis-diamino-chloro-(4-amino)benzoate-platinum(II) hydrochloride in water (15 ml) with conc. HCl (6 ml) which, after cooling at 5°–10° C., yields an analitically pure sample, decomposing at 215°–220° C.

[Pt(NH$_3$)$_2$(NH$_2$.C$_6$H$_4$—COOH)Cl]Cl

| Elementary analysis (C$_7$H$_{13}$Cl$_2$N$_3$O$_2$Pt; PM 4372) | | | |
|---|---|---|---|
| C % | H % | N % | |
| 19.23 | 3.00 | 9.61 | (found) |
| 19.36 | 3.02 | 9.41 | (calc.) |

IR (KBr, 4000–200 cm$^{-1}$): 3300–3000 (m), 2600 (d), 2460 (d), 1705 (f), 1610 (m), 1510 (d), 1235 (m), 340 (d). $^1$H-NMR (200 MHz, internal standard TMS, solvent DMSO): δ(ppm) 3.35 (q.s., 2H); 4.11 (q.s., 3H); 4.72 (q.s., 3H); 7.40 (d., J=8.5 Hz, 2 H); 7.87 (d., J=8.5 Hz, 2 H); 7.60–8.10 (s.a., 1 H, exchanges with D$_2$O) UV (H$_2$O)

| $\lambda_{max}$ (nm) | log E |
|---|---|
| 205 | 4.09 |
| 238 | 4.06 |

EXAMPLE 2

An aqueous solution of cis-diamine-chloro-(4-amino)-benzoate-platinum(II) hydrochloride is adsorbed on silica gel. By methanol elution and partial evaporation, a crystalline precipitate is separated of aquo-cis-diamino-chloro-(4-amino)benzoate-platinum(II), 1b, which is filtered and dried at room temperature under vacuum.

EXAMPLE 3

Lithium hydroxide (2 mM, 0.048 g) is added to a suspension of PABA (2 mM, 0.274 g) in water (50 ml); the mixture is kept under stirring at room temperature until a clear and colourless solution is obtained which is added, in a single batch, with cis-diaminodichloroplatinum(II) (1 mM, 0.3 g). The suspension is stirred at 50 ° C. until complete dissolution of the dichloroplatinum complex (about 1 hour); the heating is continued for a further hour. After hot filtration, the solvent is evaporated under vacuum to dryness, avoiding that the solution inner temperature exceeds 40° C. The residue is purified by repeated suspension in methanol and subsequent methanol filtration so as to obtain pure cis-diamino-chloro-(4-amino)benzoateplatinum(II) mono methanol solvate, 1C.

I claim:

1. A compound of formula (1):

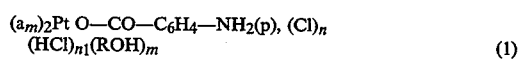

$(a_m)_2$Pt O—CO—C$_6$H$_4$—NH$_2$(p), (Cl)$_n$ (HCl)$_{n1}$(ROH)$_m$     (1)

wherein:
$a_m$ is a monovalent amine ligand which is a member selected from the group consisting of NH$_3$, linear or branched C$_1$–C$_6$ alkylamines, a cyclic amine of 3–6 carbon atoms, or the two $a_m$ groups form a linear or cyclic C$_{2-8}$-alkyl-1,2 diamine or 1,3-diamine;
R is hydrogen or C$_{1-3}$ alkyl;
$n_1$, and m are independently zero or 1 and n is 1.

2. The compound according to claim 1 wherein said amine is cyclopentylamine, cyclopropylamine, cyclohexylamine, isopropylamine, propylamine, n-pentylamine or di-isopropylamine.

3. The compound according to claim 7 wherein $a_m$ is a member selected from the group consisting of 1,2-ethylenediamine, 1,3-propylenediamine, butane-1,2-diamine, (R,S)-cyclopentane-1,2-diamine, (R,S)-cyclo-hexane-1,2-diamine, 1,1-bis-aminomethyl-cyclopentane, and 1,1-bis-aminomethylcyclohexane.

4. The compound according to claim 1 wherein R is hydrogen or methyl.

5. The compound according to claim 1 which is a member selected from the group, consisting of cis-diamino-chloro-(4-amino)benzoate-platinum(II), cis-diamino-chloro-(4-amino)benzoate-platinum (II) hydrochloride, aquo-cis-diamino-chloro-(4-amino)benzoate-platinum(II) and cis-diamino-chloro-(4-amino)benzoate-platinum(II) mono methanol solvate.

6. The process for the preparation of a compound of formula (1)

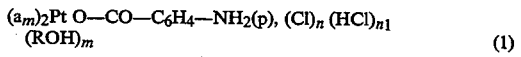

$(a_m)_2$Pt O—CO—C$_6$H$_4$—NH$_2$(p), (Cl)$_n$ (HCl)$_{n1}$ (ROH)$_m$     (1)

wherein:
$a_m$ is a monovalent amine ligand which is a member selected from the group consisting of NH$_3$, linear or branched C$_1$–C$_6$ alkylamines, a cyclic amine of 3–6 carbon atoms, or the two $a_m$ groups form a linear or cyclic C$_{2-8}$-alkyl-1,2 diamine or 1,3-diamine;
R is hydrogen or C$_{1-3}$ alkyl;
$n_1$, and m are independently zero or 1 and n is 1; which consists of reacting a dichloro-platinum(II) complex of formula (2)

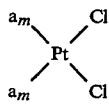

(2)

wherein $a_m$ is as defined above, with p-aminobenzoic acid or with a salt thereof, in an hydroxylated solvent to obtain a product and purifying said product by precipitation of the hydrochloride salt or by silica gel column chromatography.

7. A pharmaceutical composition for the treatment of tumors which contains an effective amount of a compound according to claim 1 together with excipients.

8. The composition according to claim 7 which is in unit dosage form, in the form of an aqueous solution, a powder, an oil, a syrup, tablet or a capsule.

* * * * *